United States Patent [19]

Vallejos et al.

[11] 4,196,299
[45] Apr. 1, 1980

[54] PROCESS FOR MANUFACTURING THIENYL-2 ACETIC ACID

[75] Inventors: Jean Claude Vallejos; Yani Christidis, both of Paris, France

[73] Assignee: Hoechst France, Puteaux, France

[21] Appl. No.: 892,435

[22] Filed: Mar. 31, 1978

[30] Foreign Application Priority Data

Apr. 19, 1977 [FR] France ............................... 77 11775

[51] Int. Cl.$^2$ ........................................... C07D 333/24
[52] U.S. Cl. ..................................................... 549/79
[58] Field of Search ..... 260/329 R, 329 AM, 332.2 A

[56] References Cited

U.S. PATENT DOCUMENTS 2,492,632  12/1949  Hartough ............................. 260/329

FOREIGN PATENT DOCUMENTS 748539  11/1944  Fed. Rep. of Germany .

OTHER PUBLICATIONS

Mongtshefte fur Chemie 95, (1964) pp. 24–29.

Primary Examiner—A. Siegel
Attorney, Agent, or Firm—Karl W. Flocks

[57] ABSTRACT

The process for manufacturing thienyl-2 acetic acid from acetylthiophene comprises condensing acetylthiophene at a temperature below 120° C. with an excess of a $C_4$ to $C_8$ aliphatic primary amine or with a cyclic amine, in the presence of an acid catalyst and removing the water formed, so as to obtain the corresponding imine. The imine is reacted with excess sulfur at a temperature equal to or below 100° C. in a basic and aprotic solvent to produce the corresponding thioamide. The thioamide is hydrolyzed by the action of an excess of a strongly alkaline base in a $C_4$ to $C_8$ alcohol or in ethylene glycol, if necessary in the presence of water, so as to obtain an alkali salt of thiophene-2 acetic acid. Finally the latter is treated with a strong acid in aqueous solution to liberate the thienyl-2 acetic acid.

11 Claims, No Drawings

PROCESS FOR MANUFACTURING THIENYL-2 ACETIC ACID

BACKGROUND OF THE INVENTION

1. Field of the Invention

The present invention relates to a process for manufacturing thienyl-2 acetic acid from acetylthiophene.

2. Description of the Prior Art

The chloride of thienyl-2 acetic acid is used in the synthesis of cephalosporins. It can be prepared easily and with good yields from thienyl-2 acetic acid by the action of thionyl chloride (U.S. Pat. No. 2,533,084). The manufacture of thienyl-2 acetic acid from thiophene is on the other hand much more delicate and although several methods have been proposed up to the present time, none has given full satisfaction. The principal methods advocated have been the following:

(a) Chloromethylation of thiophene by the action of formaldehyde in a concentrated hydrochloric acid medium (Organic Syntheses 29, 31–3 (1949)) and then conversion of the thienyl chloride obtained to thienyl-2 acetonitrile by the action of sodium cyanide and alkaline hydrolysis of the nitrile into the acid (U.S. Pat. Nos. 2,533,084 and 2,541,024).

In addition to the fact that thienyl chloride is obtained with very moderate yields, this compound is a lacrymatory product, difficult to store, and one which decomposes sometimes giving rise to violent reactions.

(b) Conversion of the thiophene into thenaldehyde by various processes, for example the action of dimethylformamide on the thiophene in the presence of POCl$_3$ (Organic Syntheses 31. 108 (1931)), then the action of sodium cyanide and ethyl chloroformate, on the thenaldehyde, followed by hydrogenation of the product obtained to form the thienyl-2 acetonitrile which is then hydrolyzed (British Pat. No. 1 122 658).

This method is relatively long and it is not economically profitable consequent upon the use of a highly enriched palladium hydrogenation catalyst.

(c) Acetylation of thiophene by acetyl chloride or acetic anhydride in the presence of various catalysts (U.S. Pat. No. 2,458,514) to obtain acetylthiophene or aceto-2 thienone or thienyl-2 methylketone and conversion of this methylketone into thienyl-2 acetamide or thienyl-2 thioacetamide by a WILLGERODT reaction, then hydrolysis of the amide (German Pat. No. 832 755).

It is known that acetophenone, in pyridine or dioxan solution, reacts with sulfur and ammonia at 150°–160° C., under pressure, to give phenylacetamide (Organic Reactions — John WILEY and SONS, Inc.—New York, N.Y. 1946—volume III, page 97), but acetylthiophene, under the same conditions, does not seem to give the corresponding amide. By lowering the temperature to 140° C. and by prolonging the reaction time, some workers (J. A. BLANCHETTE and E. V. BROWN—J. Am. Chem. Soc. 74 (1952, p. 1066–7) have however obtained yields of 43% of thienyl-2 acetamide and 53% by replacing the sulfur and the ammonia by ammonium polysulfides.

Other workers (German Pat. No. 832 755) by using sulfur and ammonium polysulfides have slightly improved these yields operating in dioxan with several heating steps between 140° and 150° C. Unfortunately, all the foregoing methods, in addition to the fact that they are operated under pressure, utilize a very large excess of sulfur and/or of ammonium polysulfide whence there result very great difficulties for separating the amide obtained from the abundant and dark sulfur products which are formed in the course of the reaction. On the other hand, it is advisable to prepare the ammonium polysulfide at the time of use by bubbling H$_2$S into a mixture of sulfur and ammonia.

Up to the present, all attempts to obtain thienyl-2 acetic acid from acetylthiophene, under moderate reaction conditions, that is to say without operating under pressure, have proved abortive. This is the case, for example, in utilising the WILLGERODT-KINDLER method in which the operation is carried out in morpholine at boiling point (BUU-HOI and NGUYEN-HOAN. Rec. Trav. Chim. 68, 5–33 (1949)).

On the other hand, ASINGER((F. ASINGER, A. SAUS, H. OFFERMANNS und F. A. DAGGA—Liebigs Ann. Chem. 723. 119-125 (1969)), has shown that with acetophenone it is possible to obtain N-n-butylthioamide of phenylacetic acid by reacting sulfur with the N-n-butylimine of acetophenone in dimethylformamide in the presence of triethylamine.

GENERAL DESCRIPTION OF THE INVENTION

Applicants have found that thienyl-2 acetic acid can be prepared from acetylthiophene by reacting a primary amine with acetylthiophene in the presence of an acid catalyst and removing the water formed so as to obtain the corresponding imine, by then converting said imine to thioamide by the action of sulfur in a basic and aprotic solvent and lastly by hydrolysing the thioamide to the acid by the action of a base in an alcohol medium and then acidification.

It is surprising that it has been possible to pass from acetylthiophene to thienyl-2 acetic acid, without operating under pressure, by a sequence of reactions under moderate temperature, similar to those used for passing from acetophenone to phenylacetic acid although up to the present methods not using pressure and useable for acetophenone had not been applied to acetylthiophene.

If the primary amine utilised is called RNH$_2$, the sequence of reactions can be portrayed diagrammatically by the following equations:

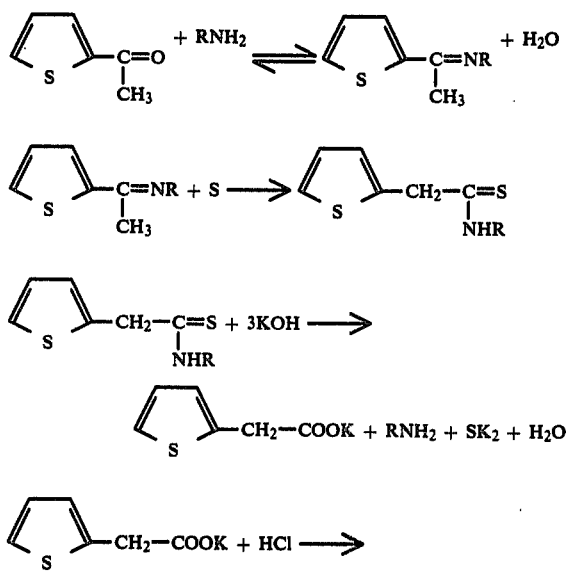

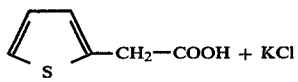
—CH$_2$—COOH + KCl

According to the invention, in the first phase of the synthesis, the reaction is carried out hot at a temperature below or equal to 120° C. of a straight or branched C$_4$ to C$_8$ aliphatic primary amine or a cyclic primary amine in excess one acetylthiophene in the presence of an acid catalyst and removing the water formed by means of a desiccating product or by azeotropic distillation with a neutral solvent.

As primary amine, it is possible to use, for example, n-butylamine, hexylamine, isoctylamine or cyclohexylamine. Cyclohexylamine or n-butylamine are preferred, the latter being an inexpensive and easily available amine. The excess of amine can reach 100%; an excess of 40% is generally quite satisfactory. The acid catalyst can be any acid, a mineral acid such as sulfuric acid, or an organic acid such as paratoluene sulfonic acid, formic acid, or acetic acid. Formic acid is advantageously used.

The dehydration can be carried out either by means of acid dehydrating agents by themselves such as acid type aluminas, or with neutral dehydrating agents such as magnesium sulfate to which a little acid catalyst is added. The alkaline dehydrating agents such as quicklime, barium oxide, or potassium carbonate are to be avoided. It is however preferable to remove the water by azeotropic distillation with a neutral solvent permitting an azeotrope to be obtained distilling below 100° C. and not to exceed the temperature of 120° C. in the reactor. Among the neutral solvents useable, may be mentioned benzene, cyclohexane, or preferably toluene.

The yields of imine can reach 90% with respect to the acetylthiophene. The N-n-butylimine of acetylthiophene

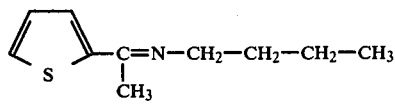

and the cyclohexylimine of acetylthiophene

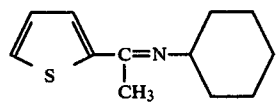

are novel intermediate industrial products. Since it is difficult to isolate them in the pure state, as they decompose in the course of distillation under vacuum, they have been identified by the NMR spectrum.

The second phase of the process according to the invention consists of reacting sulfur in excess with the imine, in a basic and aprotic solvent at a temperature at the most equal to 100° C. to obtain thioacetamide. Generally, the yield of thioacetamide increases with temperature, but it is advisable not to exceed 100° C. since the imines are relatively sensitive to temperature. In the same way, the yield increases with the proportion of sulfur, but beyond three atoms of sulfur per molecule of imine, difficulties in separating the thioacetamide from the sulfur residues are encountered. An excess of 40 to 50% with respect to the amount necessary for forming the thioacetamide appears sufficient. As basic and aprotic solvent, it is preferable to use pyridine or dimethylformamide. When dimethylformamide is used, it is advantageous to add a tertiary amine, such as triethylamine, as catalyst. Pyridine is sufficiently basic and does not need a catalyst.

N-n-butylthienyl-2 thioacetamide and N-cyclohexylthienyl-2 thioacetamide are novel intermediate industrial products; they have been identified by their NMR spectra.

The hydrolysis of thioacetamide is done at a temperature of 120° to 135° C. with solutions of a strong base, caustic soda or caustic potash in excess, either in a C$_4$ to C$_8$ aliphatic alcohol, or in ethylene glycol or ethylene glycol/water mixtures. It is preferred to use potassium hydroxide in solution in heptanol since the potassium salt of thiophene-2 acetic acid precipitates in the course of the hydrolysis and it is then possible to separate it easily by washing with water.

According to a modification of the process, before hydrolysis, the crude thioacetamide is dissolved at a temperature below 5° C. in methanol, which permits the removal of an insoluble black product, and hence a purer product can be obtained.

The aqueous solution of the alkali salt of thiophene-2 acetic acid derived from the dilution or extraction with water of the hydrolysis liquor, containing also alkali sulfides, is acidified with an acid, for example hydrochloric acid, and the thiophene-2 acetic acid is extracted by a neutral solvent like dichlorethane.

By removal by distillation of the dichlorethane, crude thiophene-2 acetic acid is obtained.

Again according to a modification of the process, the aqueous solution containing the alkali salt of the thiophene-2 acetic acid is first acidified to pH 4, filtered to separate the insoluble, then the acidification is continued to pH 2. In this way better yields of acid and a purer product are obtained.

The crude thiophene-2 acetic acid obtained can be recrystallized in heptane, hexane, or petroleum ether; it is with the latter solvent that the purest and least colored product is obtained.

It is also possible, when heptanol is used as a hydrolysis solvent, to separate the potassium salt from the thiophene-2 acetic acid by filtration, wash it with acetone, then liberate the thiophene-2 acetic acid by the action of a strong acid, but the potassium salt is difficult to filter.

As has been mentioned above, thiophene-2 acetic acid is easily converted into the acid chloride by the action of SOCl$_2$ and this chloride is used in the synthesis of cephalosporins.

DESCRIPTION OF PREFERRED EMBODIMENTS

The following examples are given by way of illustration and are not to be regarded as in any way limiting.

EXAMPLE 1

756 g (6 moles) of acetyl-thiophene and 613 g (8.4 moles) of n-butylamine are azeotropically dehydrated in 2598 g of toluene in the presence of 15 g of formic acid. It is then concentrated under vacuum and mixtures of toluene and amine are thus recovered; 1081.6 g of acetylthiophene N-n-butylamine at 90% purity are obtained, namely a yield of 89.6%.

The acetylthiophene N-n-butylamine boils at 102°–105° C. under 2 mm of mercury.

NMR spectra in carbon tetrachloride of the distilled product:

| | |
|---|---|
| $\delta = 0.65$ at 2 ppm | complex mass (7H) |
| $\delta = 2.05$ ppm | singulet (3H) |
| $\delta = 3.30$ ppm | triplet (2H) |
| $\delta = 6.65$ at 7.25 ppm | multiplet (3H) |

436 g (2.14 moles) of n-butylamine and 96 g (3 atom-grams) of sulphur in 1966 g (2 l) of pyridine are heated at 100° C. for 6 hours. After cooling to 40°–50° C., the pyridine is distilled under vacuum without exceeding 100° C. in the flask. To the oily residue obtained, 1600 ml of methanol are added and it is kept for 4 hours at 0°–5° C. The insoluble black formed is separated by filtration, then the methanol is distilled under atmospheric pressure. 422 g of thioamide in oily form is obtained.

NMR spectrum of thiophene-2 acetic acid N-n-butyl-thioamide in $CDCl_3$:

| | |
|---|---|
| $\delta = 0.5$ at 1.9 ppm | complex mass (7H) |
| $\delta = 3.5$ ppm | quadruplet (2H) |
| $\delta = 4.1$ ppm | singulet (2H) |
| $\delta = 6.6$ at 7.2 ppm | multiplet (3H) |
| $\delta = 8.7$ ppm | wide mass (1H) |

To the thioacetamide obtained, 2 liters of heptanol and 448 g (8 moles) of potash are added, and it is heated for 1 hour at 135° C. After cooling to ambient temperature, 2 liters of water are added with stirring. The lower aqueous phase is separated and the organic layer is washed with 500 ml of water. The collected aqueous phases are washed with 200 ml of toluene then acidified to pH 4 at 5° C. with concentrated hydrochloric acid; the insoluble which is formed is filtered and the acidification is then continued at 5° C. to pH 2.

The aqueous solution and the precipitate are then extracted with 500 ml of dichlorethane. The organic phases are concentrated under atmospheric pressure, then under vacuum; 173 g of crude thienyl-2 acetic acid are obtained, namely a yield of 56.9% with respect to the imine.

By recrystallisation in petroleum ether, 135 g of thiophene acetic acid are obtained, titrating 99.5% by acidimetry.

MP (capillary tube) = 63°–64° C.

| Elementary analysis: | Calculated | Found |
|---|---|---|
| C% | 50.68 | 50.5 |
| H% | 4.25 | 4.29 |
| S% | 22.55 | 22.4 |

EXAMPLE 2

295 g (1.5 mole) of acetylthiophene N-n-butylimine of 92% purity and 72 g (2.25 atom-grams) of sulphur in 1474.5 g (1.5 liters) of pyridine are heated for 6 hours at 100° C. The pyridine is then distilled under vacuum without exceeding 100° C. in the flask. The residue diluted in 1800 ml of heptanol supplemented with 336 g (6 moles) of KOH is kept for 1 hour at 135° C. After cooling, the potassium salt is extracted with 1500 ml plus 500 ml of water; the aqueous phases are washed with toluene then acidified at 5° C. by concentrated HCl to pH 2, in the presence of 500 ml of dichlorethane; the aqueous phase is again extracted with 750 ml of dichlorethane.

By distillation of the diclorethane under vacuum, the organic phases provide 142 g of crude thienyl-2 acetic acid titrating 84% by acidimetry. Yield 56% with respect to the imine.

EXAMPLE 3

378 g (3 moles) of acetylthiophene, 594 g (6 moles) of cyclohexylamine and 6 ml of formic acid are azeotropically dehydrated by means of 1 liter of toluene. When all the water has been removed, the solution is cooled and the toluene and excess amine are removed under reduced pressure of 18 mm of mercury, without exceeding 120° C. in the reactor. In this way, 630 g of acetyl-thiophene N-cyclohexylimine are obtained, titrating 94.5% by gas phase chromatography, namely a yield of 97%. NMR spectrum in carbon tetrachloride

| | |
|---|---|
| $\delta = 1$ to 2 ppm | complex mass (10H) |
| $\delta = 2.15$ ppm | singulet (3H) |
| $\delta = 3.40$ ppm | multiplet (1H) |
| $\delta = 6.70$ to 7.30 ppm | multiplet (3H) |

219 g (1 mole) of N-cyclohexylimine and 48 g (1.5 atom-grams) of sulphur in 500 ml of dimethylformamide were heated for 6 hours at 100° C. After cooling, 2 liters of water were added, and it was extracted twice with 1.5 liters of chloroform.

After concentration of the chloroform solutions, 2 liters of methanol were added to the residue and it was kept for 48 hours at 5° C. After filtration and concentration, 174 g of thiophene 2 acetic acid N-cyclohexylthi-oamide were obtained.

NMR spectrum of thiophene-2 acetic acid N-cyclohexylthioamide in carbon tetrachloride.

| | |
|---|---|
| $\delta = 0.59$ to 2.25 ppm | complex mass (10H) |
| $\delta = 4.15$ ppm | singulet (2H) |
| $\delta = 4.25$ ppm | wide mass (1H) |
| $\delta = 6.65$ to 7.25 ppm | multiplet (3H) |

1200 ml of heptanol and 224 g (4 moles) of potash were added to the thioamide obtained and it was kept for one hour at 130°–135° C. After cooling to ambient temperature, 1 liter of water was added, it was decanted and the organic phase extracted three times with 400 ml of water. The aqueous phases were collected and washed with 600 ml of chloroform and 400 ml of ether, then acidified to pH 1.5 in the presence of 800 ml of ether. By concentration of the ether solutions previously dried over magnesium sulphate, 64 g of thiophene-2 acetic acid were obtained, namely a yield of 45%.

It is self-evident that the present invention has only been described purely by way of explanation, and that this description is in no way limiting and that any useful modification on the level of equivalents could be introduced therein without departing from its scope as defined by the appended claims.

We claim:

1. Process for manufacturing thienyl-2 acetic acid from acetylthiophene comprising, condensing acetylthiophene at a temperature below 120° C. with an excess of a $C_4$ to $C_8$ aliphatic primary amine or with a cyclic amine, in the presence of an acid catalyst selected from the group consisting of formic acid and acetic acid and removing the water formed, so as to obtain the corresponding imine, reacting said imine with excess sulfur at a temperature equal to or below 100° C. in a basic and aprotic solvent to produce the corresponding thioamide, hydrolysing said thioamide by the action of an excess of a strongly alkaline base in a $C_4$ to $C_8$ alcohol or in ethylene glycol, if necessary in the presence of water, so as to obtain an alkali salt of thiophene-2 acetic acid, and finally treating the latter with a strong acid in aqueous solution to liberate the thenyl-2 acetic acid.

2. Manufacturing process according to claim 1, wherein in the condensation of the acetyl-thiophene with the primary amine, the water formed is removed by azeotropic distillation by means of a neutral solvent so that the temperature does not exceed 105° C. in the reaction vessel.

3. Manufacturing process according to claim 1, wherein before hydrolysis, the thioamide is stirred at a temperature below 5° C. with methanol and separating the insoluble product formed.

4. Manufacturing process according to claim 1, wherein the acidification of the aqueous solution of the alkali salt of the thiophene-2 acetic acid is first carried out to pH 4, the insoluble substance is separated, and then the acidification is terminated up to pH 2.

5. Manufacturing process according to claim 1, wherein the aliphatic primary amine used is n-butylamine or cyclohexylamine.

6. Manufacturing process according to claim 1, wherein in the condensation of the primary amine with the acetylthiophene, the dehydration solvent is toluene.

7. Manufacturing process according to claim 1, wherein the basic and aprotic solvent used for the reaction of the sulfur with the imine is pyridine.

8. Manufacturing process according to claim 1, wherein the basic and aprotic solvent used for the reaction of the sulfur on the imine is dimethylformamide, if necessary in the presence of triethylamine.

9. Manufacturing process according to claim 1, wherein the hydrolysis of the thioacetamide is carried out by potash dissolved in heptanol.

10. Manufacturing process according to claim 10, wherein the potassium salt of thienyl-2 acetic acid which precipitates is taken up again in water.

11. Manufacturing process according to claim 1, wherein the acid catalyst used for the condensation of the primary amine with acetylthiophene is formic acid.

* * * * *